(12) United States Patent
Keenan

(10) Patent No.: US 6,201,157 B1
(45) Date of Patent: Mar. 13, 2001

(54) METHOD FOR PRODUCTION OF PHENOL AND ACETONE BY DECOMPOSITION OF CUMENE HYDROPEROXIDE

(75) Inventor: Scott R. Keenan, Marlton, NJ (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 0 days.

(21) Appl. No.: 09/480,206

(22) Filed: Jan. 10, 2000

(51) Int. Cl.⁷ ................................................. C07C 37/08
(52) U.S. Cl. .................... 568/798; 568/754; 568/385; 568/311
(58) Field of Search ................................. 568/311, 385, 568/798, 485, 741, 768, 754

(56) References Cited

U.S. PATENT DOCUMENTS

| | | | |
|---|---|---|---|
| 4,267,379 | * 5/1981 | Austin et al. | 568/385 |
| 5,254,751 | 10/1993 | Zakoshansky | 568/798 |
| 5,491,268 | 2/1996 | Cipullo | 568/758 |

* cited by examiner

*Primary Examiner*—Sreeni Padmanabham
(74) *Attorney, Agent, or Firm*—Robert A. Koons, Jr.; Matthew P. McWilliams; Pepper Hamilton LLP

(57) ABSTRACT

An improved method for production of phenol and acetone by decomposition of cumene hydroperoxide in the presence of an acidic catalyst to phenol and acetone, wherein the improvement comprises neutralization of the acidic catalyst after substantial completion of the decomposition by addition of a substituted amine.

9 Claims, No Drawings

METHOD FOR PRODUCTION OF PHENOL AND ACETONE BY DECOMPOSITION OF CUMENE HYDROPEROXIDE

BACKGROUND OF THE INVENTION

1. Field of the Invention

The present invention relates to an improved method for production of phenol and acetone by decomposition of cumene hydroperoxide to phenol, acetone, and α-methylstyrene in the presence of an acidic catalyst. The improvement comprises neutralization of the acidic catalyst after substantial completion of the decomposition by addition of a substituted amine.

2. Related Background Art

One of the predominant commercial processes for manufacture of phenol is the cumene oxidation process, in which cumene is oxidized in air to produce cumene hydroperoxide (CHP). The CHP is then cleaved to phenol and acetone in the presence of an acidic catalyst. This process also produces α-methylstyrene (AMS), along with other byproducts, including acetophenone, dimethylphenylcarbinol, and cumylphenols. Typically, the acidic catalyst is a strong, and not heavily corrosive inorganic acid, such as sulfuric or phosphoric acid. The acidic catalyst must be removed or neutralized to prevent further, unwanted reactions in the downstream purification steps that produce the phenol and acetone products.

Typically, commercial processes for manufacture of phenol from CHP use inorganic bases, ion exchange resins, or a combination thereof to remove acidity from the crude product stream. Since ion exchange resins are temperature sensitive, the crude product stream must be cooled substantially prior to contact with the resin. The need to cool the product stream increases energy costs significantly because the crude product stream must then be re-heated prior to downstream purification operations. A further drawback of ion exchange resins is that they must be regenerated frequently, a labor-intensive and costly process which also results in formation of large amounts of aqueous waste. Moreover, ion exchange resins give a highly variable final pH in the crude product stream, adversely affecting final product yields, and can also release alkali salts which cause fouling of equipment.

The use of a strong base, such as sodium hydroxide or potassium hydroxide to neutralize the acidic catalyst is not desirable because it is difficult to achieve accurate pH control in a neutralization reaction between a strong acid and a strong base. Moreover, metal hydroxides generate salts that have a propensity to deposit on heat exchange surfaces, causing fouling and decreasing efficiency.

The use of ammonia to neutralize the acidic catalyst is disclosed in U.S. Pat. No. 5,254,751 to Zakoshansky. In the process described in this reference, neutralization with ammonia is performed during the CHP decomposition, rather than after the decomposition. The disclosure states that the ammonium salts produced from addition of ammonia to the reaction mixture act as acidic catalysts for the remainder of the CHP decomposition reaction. This reference suggests that hydrazine and alkylamines having one to five carbon atoms are suitable for neutralization during CHP decomposition, but that ammonia is preferred, especially for neutralizing sulfuric acid. Zakoshansky also suggests a maximum operating temperature of 110° C.

SUMMARY OF THE INVENTION

The present invention is directed to an improved method for production of phenol and acetone from cumene hydroperoxide by decomposition of cumene hydroperoxide in the presence of an acidic catalyst, wherein the improvement comprises neutralization of the acidic catalyst after substantial completion of the decomposition by addition of a substituted amine selected from the group consisting of: (i) a secondary or tertiary amine having from 4 to 21 carbon atoms and not having hydrolytically unstable substituents or acidic substituents; and (ii) a primary amine of formula

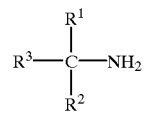

wherein $R^1$ and $R^2$ are independently hydrogen or $C_1$–$C_{12}$ alkyl, and $R^3$ is hydrogen, $C_1$–$C_{12}$ alkyl or $C_1$–$C_{12}$ alkyl substituted by hydroxyl, amino or dimethylamino, provided that at least two of $R^1$, $R^2$ and $R^3$ are not hydrogen.

DETAILED DESCRIPTION OF THE INVENTION

The term "alkyl" is used herein to refer to a saturated acyclic hydrocarbyl substituent group which may be linear or branched. The term "alkylene" is used herein to refer to an acyclic hydrocarbyl substituent group having at least one carbon-carbon double bond, and which may be linear or branched. The term "secondary or tertiary amine" is used herein to refer to an amine in which there is at least one nitrogen atom directly bonded to at least two carbon atoms.

The term "acidic substituents" is used herein to refer to substituents having a pKa value in aqueous media of less than about 5. Examples of acidic substituents include the acid forms of carboxylates, nitrates, phosphates, phosphonates, sulfates and sulfonates. The term "hydrolytically unstable substituents" is used herein to refer to those substituents that undergo substantial hydrolysis and/or condensation reactions at a pH in the range from about 3.5 to about 1.5 and a temperature in the range from about 30° C. to about 180° C. in a period of about two hours. Examples of hydrolytically unstable groups are esters, anhydrides, amides, acid halides, amidines, aminals, enamines, aldehydes, ethers, acetals, hemi-acetals, ketals, hemi-ketals, epoxides and alkynes. Preferably, a substituted amine employed in the present invention contains no elements other than carbon, hydrogen, nitrogen and oxygen, and no functional groups containing nitrogen or oxygen other than amine and hydroxyl groups.

The substituted amine employed in the present invention allows neutralization of product streams from decomposition of cumene hydroperoxide at elevated temperatures with minimal formation of byproducts from reactions between the amine and organic constituents of the product stream, e.g., acetone. Performing the neutralization at elevated temperatures, i.e., temperatures near the normal process temperature for decomposition of the hydroperoxide, eliminates the need to cool the process stream prior to neutralization, and then reheat prior to performing purification operations. The preferred temperature range for the neutralization process of this invention is from about 30° C. to about 180° C., more preferably from about 60° C. to about 160° C., and most preferably from about 120° C. to about 160° C.

Neutralization with relatively unsubstituted amines which are highly basic, relatively unsubstituted and sterically relatively unhindered, as suggested in the literature, e.g., ammonia, is not efficient, especially at elevated temperatures. This is believed to be due to consumption of the amine in reactions with acetone or other components of the process stream. As shown below in Example 33, addition of ammonium hydroxide to a typical product mixture at 140.3° C. produces a much smaller change in pH than the same amount added at 22.5° C., indicating that a substantial amount of the ammonia is consumed in side reactions. Even at 100.2° C., the pH is significantly lower than that observed at 22.5° C. Addition of the relatively unsubstituted amines DYTEK®-A, hexamethylene diamine, or n-propylamine also produces a much smaller change in pH at high temperatures, as shown below in Examples 1–3.

In contrast, the amines employed in the present invention exhibit a final pH at a high temperature that is much closer to the final pH observed at low temperature. These amines are more sterically hindered or are more highly substituted on the nitrogen. Without being bound to theory, it is believed that these amines do not undergo reactions with organic constituents of the product stream as readily due to the aforementioned characteristics, and are thus more efficient neutralizing agents, especially at high temperatures.

The method of the present invention allows better control of the post-neutralization pH of the product stream than conventional methods, especially when the neutralization is conducted at elevated temperatures. Preferably, the target final pH is in the range from about 2.0 to about 3.5, most preferably from about 2.2 to about 2.8.

In a preferred embodiment of the invention, the secondary or tertiary amine is selected from the group consisting of

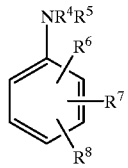

wherein $R^4$ and $R^5$ are independently hydrogen or methyl, and $R^6$, $R^7$ and $R^8$ are independently hydrogen or $C_1$–$C_4$ alkyl;

wherein $R^9$ and $R^{10}$ are independently $C_1$–$C_{12}$ alkyl, $C_2$–$C_{12}$ alkyl substituted by hydroxyl, amino or dimethylamino, $C_3$–$C_7$ alkylene or $R^9$ and $R^{10}$ join with $NR^{11}$ to form a cyclic aliphatic amine having from 5 to 7 ring atoms, e.g., hexamethyleneimine, and $R^{11}$ is hydrogen, $C_2$–$C_{12}$ alkyl, $C_2$–$C_{12}$ alkyl substituted by hydroxyl, $C_5$–$C_6$ cycloalkyl or $C_3$–$C_7$ alkylene, provided that $R^9$, $R^{10}$ and $R^{11}$ taken together contain at least six carbon atoms; and

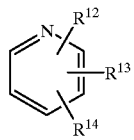

wherein $R^{12}$, $R^{13}$ and $R^{14}$ are independently hydrogen or $C_1$–$C_4$ alkyl.

In another preferred embodiment of the invention, the substituted amine is

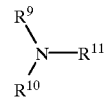

wherein $R^9$ and $R^{10}$ are independently $C_2$–$C_6$ alkyl or $C_2$–$C_6$ alkyl substituted by hydroxyl, or $R^9$ and $R^{10}$ join with $NR^{11}$ to form a cyclic aliphatic amine having from 6 to 7 ring atoms; and $R^{11}$ is hydrogen, $C_2$–$C_6$ alkyl or $C_2$–$C_6$ alkyl substituted by hydroxyl. The substituted amine contains at least six carbon atoms. Preferred amines in this embodiment of the invention are triethylamine, tri-n-propylamine, triisopropylamine, triisopropanolamine, di-n-propylamine, di-isopropylamine, di-n-butylamine, di-n-hexylamine and hexamethyleneimine. More preferably, $R^9$, $R^{10}$ and $R^{11}$ are independently $C_2$–$C_6$ alkyl or $C_2$–$C_6$ alkyl substituted by hydroxyl. Particularly preferred amines in this embodiment of the invention are triethylamine, tri-n-propylamine, triisopropylamine and triisopropanolamine. Most preferably, $R^9$, $R^{10}$ and $R^{11}$ are independently $C_3$–$C_6$ alkyl or $C_3$–$C_6$ alkyl substituted by hydroxyl. The most preferred amines in this embodiment are tri-n-propylamine, triisopropylamine and triisopropanolamine.

In another preferred embodiment of the invention, the substituted amine is

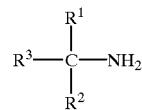

wherein $R^1$ and $R^2$ are independently $C_1$–$C_9$ alkyl, and $R^3$ is $C_1$–$C_9$ alkyl or $C_1$–$C_9$ alkyl substituted by hydroxyl or amino. It is preferred that $R^1$ and $R^2$ are independently $C_1$–$C_9$ alkyl, and $R^3$ is $C_2$–$C_9$ alkyl. Preferred amines include tert-amylamine (1,1-dimethylpropylamine) and tert-octylamine (1,1,3,3tetramethylbutylamine). It is further preferred that $R^1$ and $R^2$ are methyl and $R^3$ is $C_3$–$C_9$ alkyl. Most preferably, $R^1$ and $R^2$ are methyl and $R^3$ is $C_5$–$C_9$ alkyl. The most preferred amine in this embodiment of the invention is tert-octylamine.

In another preferred embodiment of the invention, the substituted amine is selected from the group consisting of a 2,6-dialkyl aniline, N-methyl aniline and N,N-dimethyl aniline. Particularly preferred anilines of this type are 2,6-dimethyl aniline, 2,6-diethyl aniline and N-methylaniline.

Other organic bases are suitable for use in the method of the present invention, although not preferred. For example, tetraalkylammonium hydroxides, where the alkyl groups independently contain from one to ten carbon atoms, are efficient neutralizing agents under the conditions described herein, as illustrated by Examples 29 and 30.

The following Examples are intended solely to illustrate certain preferred embodiments of the invention, and not to limit the invention.

EXAMPLES

Example 1

Temperature Effects on Neutralization of Crude Product with "DYTEK® A" Amine.

A ½' stainless steel tube capped at one end, with a ¼" stainless steel ball valve at the other end, was used as a static reactor for the elevated-temperature runs. At temperatures above about 80° C., the exit of the valve was sealed with a septum cap which was secured with wire. The tube was sufficiently long so that a 10 mL charge of crude product at room temperature left about 1 cm of void space in the tube itself. The crude product had an acid content of 34-38 ppm as sulfuric acid. A solution of 1% 2-methyl-1,5-pentanediamine (available from Aldrich Chemical Co. under the name "DYTEK® A") in water was added via a gas-tight syringe with a needle sufficiently long to reach the center of the void space, with vigorous shaking and mixing for 30 seconds after addition. For the low-temperature (22.5° C.) runs, the solutions were mixed in a glass beaker for pH measurement. The results of the pH measurement for each run are summarized in the following table, along with the amount of amine added in that run, and the temperature of the run in ° C. (T). The change in pH with temperature is reported as "% off target", which is the pH of the low-temperature run minus the pH of the higher-temperature run divided by the pH of the low-temperature run, expressed as a percentage.

| T | μL 1% DYTEK® A | pH | % off target |
|---|---|---|---|
| 22.5 | 40.0 | 2.70 | 0.0 |
| 100.2 | 40.0 | 2.12 | 21.5 |
| 140.3 | 40.0 | 1.29 | 52.2 |
| 22.5 | 40.0 | 2.64 | 0.0 |
| 100.5 | 40.0 | 1.99 | 24.6 |
| 140.5 | 40.0 | 1.20 | 54.5 |
| 22.5 | 40.0 | 2.60 | 0.0 |
| 100.3 | 40.0 | 1.98 | 23.8 |
| 140.7 | 40.0 | 1.13 | 56.5 |

Example 2

Temperature Effects on Neutralization of Crude Product with Hexamethylenediamine.

The method and apparatus described in Example 1 were used to determine temperature effects on neutralization of crude product with an aqueous solution of hexamethylenediamine (HMDA). Results of pH measurement for each run are presented in the following table:

| T | μL 0.5% HMDA | pH | % off target |
|---|---|---|---|
| 22.5 | 80.0 | 2.74 | 0.0 |
| 100.5 | 80.0 | 2.26 | 17.5 |
| 140.5 | 80.0 | 1.40 | 48.9 |

Example 3

Temperature Effects on Neutralization of Crude Product with n-Propylamine.

The method and apparatus described in Example 1 were used to determine temperature effects on neutralization of crude product with an aqueous solution of n-propylamine. Results of pH measurement for each run are presented in the following table:

| T | μL 0.3% n-propylamine | pH | % off target |
|---|---|---|---|
| 22.5 | 60.0 | 2.48 | 0.0 |
| 100.5 | 60.0 | 1.91 | 23.0 |
| 140.5 | 60.0 | 0.92 | 62.9 |

Example 4

Temperature Effects on Neutralization of Crude Product with iso- Propylamine.

The method and apparatus described in Example 1 were used to determine temperature effects on neutralization of crude product with an aqueous solution of iso-propylamine. Results of pH measurement for each run are presented in the following table:

| T | μL 0.3% iso-propylamine | pH | % off target |
|---|---|---|---|
| 22.5 | 80.0 | 2.64 | 0.0 |
| 100.5 | 80.0 | 2.26 | 14.4 |
| 140.5 | 80.0 | 1.94 | 26.5 |

Example 5

Temperature Effects on Neutralization of Crude Product with tert-Amylamine.

The method and apparatus described in Example 1 were used to determine temperature effects on neutralization of crude product with an aqueous solution of tert-amylamine ("t-amylamine). Results of pH measurement for each run are presented in the following table:

| T | μL 1.0% t-amylamine | pH | % off target |
|---|---|---|---|
| 22.5 | 50.0 | 2.84 | 0.0 |
| 100.5 | 50.0 | 2.71 | 4.6 |
| 140.5 | 50.0 | 2.54 | 10.6 |

Example 6

Temperature Effects on Neutralization of Crude Product with tert-octylamine.

The method and apparatus described in Example 1 were used to determine temperature effects on neutralization of crude product with an a cumene solution of tert-octylamine ("t-octylamine"). Results of pH measurement for each run are presented in the following table:

| T | μL 1.0% t-octylamine | pH | % off target |
|---|---|---|---|
| 22.5 | 70.0 | 2.61 | 0.0 |
| 100.2 | 70.0 | 2.51 | 3.8 |
| 140.3 | 70.0 | 2.35 | 10.0 |

Example 7

Temperature Effects on Neutralization of Crude Product with Bis(hexamethylene)triamine ("BHMT").

The method and apparatus described in Example 1 were used to determine temperature effects on neutralization of crude product with an aqueous solution of BHMT. Results of pH measurement for each run are presented in the following table:

| T | μL 0.5% BHMT | pH | % off target |
|---|---|---|---|
| 22.5 | 120.0 | 2.64 | 0.0 |
| 100.5 | 120.0 | 2.48 | 6.1 |
| 140.5 | 120.0 | 1.81 | 31.4 |

Example 8
Temperature Effects on Neutralization of Crude Product with DYTEK®-EP.

The method and apparatus described in Example 1 were used to determine temperature effects on neutralization of crude product with an aqueous solution of 1,3-diaminopentane (available from Aldrich Chemical Co. under the name DYTEK®-EP). Results of pH measurement for each run are presented in the following table:

| T | μL 0.5% DYTEK ® EP | pH | % off target |
|---|---|---|---|
| 22.5 | 80.0 | 2.67 | 0.0 |
| 100.5 | 80.0 | 2.26 | 15.4 |
| 140.5 | 80.0 | 1.98 | 25.8 |

Example 9
Temperature Effects on Neutralization of Crude Product with Di-n-Propylamine.

The method and apparatus described in Example 1 were used to determine temperature effects on neutralization of crude product with a cumene solution of Di-n-propylamine ("Di-n-PrNH2"). Results of pH measurement for each run are presented in the following table:

| T | μL 1.0% Di-n-PrNH2 | pH | % off target |
|---|---|---|---|
| 22.5 | 60.0 | 2.52 | 0.0 |
| 100.3 | 60.0 | 2.37 | 6.0 |
| 140.5 | 60.0 | 2.16 | 14.3 |

Example 10
Temperature Effects on Neutralization of Crude Product with Di-n-Butylamine.

The method and apparatus described in Example 1 were used to determine temperature effects on neutralization of crude product with a cumene solution of Di-n-butylamine ("Di-n-BuNH2"). Results of pH measurement for each run are presented in the following table:

| T | μL 1.0% Di-n-BuNH2 | pH | % off target |
|---|---|---|---|
| 22.5 | 80.0 | 2.70 | 0.0 |
| 100.2 | 80.0 | 2.53 | 6.3 |
| 140.5 | 80.0 | 2.34 | 13.3 |

Example 11
Temperature Effects on Neutralization of Crude Product with Hexamethyleneimine ("HMI").

The method and apparatus described in Example 1 were used to determine temperature effects on neutralization of crude product with an aqueous solution of HMI. Results of pH measurement for each run are presented in the following table:

| T | μL 1.0% HMI | pH | % off target |
|---|---|---|---|
| 22.5 | 50.0 | 2.67 | 0.0 |
| 100.5 | 50.0 | 2.58 | 3.4 |
| 140.5 | 50.0 | 2.25 | 15.7 |

Example 12

Temperature Effects on Neutralization of Crude Product with N-Methylaniline.

The method and apparatus described in Example 1 were used to determine temperature effects on neutralization of crude product with a cumene solution of N-methylaniline ("N-MeAn"). Results of pH measurement for each run are presented in the following table:

| T | μL 3.0% N-MeAn | pH | % off target |
|---|---|---|---|
| 22.5 | 70.0 | 2.66 | 0.0 |
| 100.3 | 70.0 | 2.67 | −0.4 |
| 140.5 | 70.0 | 2.56 | 3.8 |

Example 13

Temperature Effects on Neutralization of Crude Product with Aniline.

The method and apparatus described in Example 1 were used to determine temperature effects on neutralization of crude product with a cumene solution of aniline. Results of pH measurement for each run are presented in the following table:

| T | μL 3.0% aniline | pH | % off target |
|---|---|---|---|
| 22.5 | 80.0 | 2.65 | 0.0 |
| 100.3 | 80.0 | 2.14 | 19.2 |
| 140.5 | 80.0 | 1.78 | 32.8 |

Example 14

Temperature Effects on Neutralization of Crude Product with 1,4-Phenylenediamine ("1,4-PDA").

The method and apparatus described in Example 1 were used to determine temperature effects on neutralization of crude product with an aqueous solution of 1,4-PDA. Results of pH measurement for each run are presented in the following table:

| T | μL 0.4% 1,4-PDA | pH | % off target |
|---|---|---|---|
| 22.5 | 100.0 | 2.53 | 0.0 |
| 100.5 | 100.0 | 1.69 | 33.2 |
| 140.5 | 100.0 | 1.46 | 42.3 |

Example 15

Temperature Effects on Neutralization of Crude Product with m-Toluidine.

The method and apparatus described in Example 1 were used to determine temperature effects on neutralization of crude product with a cumene solution of m-toluidine. Results of pH measurement for each run are presented in the following table:

| T | μL 2.1% m-toluidine | pH | % off target |
|---|---|---|---|
| 22.5 | 80.0 | 2.59 | 0.0 |
| 100.3 | 80.0 | 1.93 | 25.5 |
| 140.5 | 80.0 | 1.34 | 48.3 |
| 140.5 | 80.0 | 1.37 | 47.1 |

Example 16

Temperature Effects on Neutralization of Crude Product with o-Toluidine.

The method and apparatus described in Example 1 were used to determine temperature effects on neutralization of crude product with a cumene solution of o-toluidine. Results of pH measurement for each run are presented in the following table:

| T | μL 3.1% o-toluidine | pH | % off target |
|---|---|---|---|
| 22.5 | 70.0 | 2.59 | 0.0 |
| 100.3 | 70.0 | 2.24 | 13.5 |
| 140.5 | 70.0 | 1.81 | 30.1 |

Example 17

Temperature Effects on Neutralization of Crude Product with 2-Ethylaniline.

The method and apparatus described in Example 1 were used to determine temperature effects on neutralization of crude product with a cumene solution of 2-ethylaniline ("2-EtAn"). Results of pH measurement for each run are presented in the following table:

| T | μL 3.0% 2-EtAn | pH | % off target |
|---|---|---|---|
| 22.5 | 80.0 | 2.61 | 0.0 |
| 100.3 | 80.0 | 2.18 | 16.5 |
| 140.5 | 80.0 | 1.76 | 32.6 |

Example 18

Temperature Effects on Neutralization of Crude Product with 2-n-Propylaniline ("2-n-PrAn").

The method and apparatus described in Example 1 were used to determine temperature effects on neutralization of crude product with a cumene solution of 2-n-PrAn. Results of pH measurement for each run are presented in the following table:

| T | μL 3.2% 2-n-PrAn | pH | % off target |
|---|---|---|---|
| 22.5 | 90.0 | 2.56 | 0.0 |
| 100.3 | 90.0 | 2.18 | 14.8 |
| 140.5 | 90.0 | 1.80 | 29.7 |

Example 19

Temperature Effects on Neutralization of Crude Product with 2-iso-Propylaniline ("2-i-PrAn").

The method and apparatus described in Example 1 were used to determine temperature effects on neutralization of crude product with a cumene solution of 2-i-PrAn. Results of pH measurement for each run are presented in the following table:

| T | μL 4.3% 2-i-PrAn | pH | % off target |
|---|---|---|---|
| 22.5 | 60.0 | 2.54 | 0.0 |
| 100.3 | 60.0 | 2.18 | 14.2 |
| 140.5 | 60.0 | 1.77 | 30.3 |

Example 20

Temperature Effects on Neutralization of Crude Product with Pyridine.

The method and apparatus described in Example 1 were used to determine temperature effects on neutralization of crude product with a cumene solution of pyridine. Results of pH measurement for each run are presented in the following table:

| T | μL 1.0% pyridine | pH | % off target |
|---|---|---|---|
| 22.5 | 130.0 | 2.51 | 0.0 |
| 100.2 | 130.0 | 2.39 | 4.8 |
| 140.3 | 130.0 | 2.43 | 3.2 |

Example 21

Temperature Effects on Neutralization of Crude Product with Tri-n-Propylamine.

The method and apparatus described in Example 1 were used to determine temperature effects on neutralization of crude product with a cumene solution of tri-n-propylamine ("Tri-n-PrNH2"). Results of pH measurement for each run are presented in the following table:

| T | μL 1.0% Tri-n-PrNH2 | pH | % off target |
|---|---|---|---|
| 22.5 | 60.0 | 2.53 | 0.0 |
| 100.3 | 60.0 | 2.41 | 4.7 |
| 140.5 | 60.0 | 2.38 | 5.9 |

Example 22
Temperature Effects on Neutralization of Crude Product with Tni-iso-Propylamine.

The method and apparatus described in Example I were used to determine temperature effects on neutralization of crude product with a cumene solution of tri-iso-propylamine ("Tri-i-PrNH2"). Results of pH measurement for each run are presented in the following table:

| T | μL 1.0% Tri-i-PrNH2 | pH | % off target |
|---|---|---|---|
| 22.5 | 70.0 | 2.60 | 0.0 |
| 100.3 | 70.0 | 2.44 | 6.2 |
| 140.5 | 70.0 | 2.38 | 8.5 |

Example 23
Temperature Effects on Neutralization of Crude Product with Triisopropanolamine ("TIPA").

The method and apparatus described in Example 1 were used to determine temperature effects on neutralization of crude product with an aqueous solution of TIPA. Results of pH measurement for each run are presented in the following table:

| T | μL 1.14% TIPA | pH | % off target |
|---|---|---|---|
| 22.5 | 70.0 | 2.65 | 0.0 |
| 100.5 | 70.0 | 2.53 | 4.5 |
| 140.5 | 70.0 | 2.50 | 5.7 |

Example 24
Temperature Effects on Neutralization of Crude Product with 2,6-Dimethylaniline ("2,6-Di-MeAn").

The method and apparatus described in Example 1 were used to determine temperature effects on neutralization of crude product with a cumene solution of 2,6-Di-MeAn. Results of pH measurement for each run are presented in the following table:

| T | μL 5.0% 2,6-Di-MeAn | pH | % off target |
|---|---|---|---|
| 22.5 | 80.0 | 2.64 | 0.0 |
| 100.3 | 80.0 | 2.65 | −0.4 |
| 140.7 | 80.0 | 2.65 | −0.4 |

Example 25
Temperature Effects on Neutralization of Crude Product with 2,6-Diethylaniline ("2,6-Di-EtAn").

The method and apparatus described in Example 1 were used to determine temperature effects on neutralization of crude product with a cumene solution of 2,6-Di-EtAn. Results of pH measurement for each run are presented in the following table:

| T | μL 8.5% 2,6-Di-EtAn | pH | % off target |
|---|---|---|---|
| 22.5 | 80.0 | 2.63 | 0.0 |
| 100.3 | 80.0 | 2.78 | −5.7 |
| 140.7 | 80.0 | 2.70 | −2.7 |

Example 26
Temperature Effects on Neutralization of Crude Product with 2,5-Di-tert-butylaniline ("2,5-Di-tBuAn").

The method and apparatus described in Example 1 were used to determine temperature effects on neutralization of crude product with a cumene solution of 2,5-Di-tBuAn. Results of pH measurement for each run are presented in the following table:

| T | μL 5.6% 2,5-Di-tBuAn | pH | % off target |
|---|---|---|---|
| 22.5 | 70.0 | 2.49 | 0.0 |
| 100.3 | 70.0 | 2.18 | 12.4 |
| 140.7 | 70.0 | 1.71 | 31.3 |

Example 27
Temperature Effects on Neutralization of Crude Product with 2,6-Diisopropylaniline ("2,6-Di-iPrAn").

The method and apparatus described in Example 1 were used to determine temperature effects on neutralization of crude product with a cumene solution of 2,6-Di-iPrAn. Results of pH measurement for each run are presented in the following table:

| T | μL 15.0% 2,6-Di-iPrAn | pH | % off target |
|---|---|---|---|
| 22.5 | 80.0 | 2.87 | 0.0 |
| 100.3 | 80.0 | 2.92 | −1.7 |
| 140.7 | 80.0 | 2.86 | 0.3 |

Example 28
Temperature Effects on Neutralization of Crude Product with Di-n-Hexyl amine.

The method and apparatus described in Example 1 were used to determine temperature effects on neutralization of crude product with a cumene solution of di-n-hexylamine ("Di-n-HexNH2"). Results of pH measurement for each run are presented in the following table:

| T | μL 1.0% Di-n-HexNH2 | pH | % off target |
|---|---|---|---|
| 22.5 | 110.0 | 2.57 | 0.0 |
| 100.3 | 110.0 | 2.44 | 5.1 |
| 140.7 | 110.0 | 2.21 | 14.0 |

Example 29
Temperature Effects on Neutralization of Crude Product with Tetramethylammonium Hydroxide ("TMAH").

The method and apparatus described in Example 1 were used to determine temperature effects on neutralization of crude product with an aqueous solution of TMAH. Results of pH measurement for each run are presented in the following table:

| T | μL 0.7% TMAH | pH | % off target |
|---|---|---|---|
| 22.5 | 50.0 | 2.56 | 0.0 |
| 100.3 | 50.0 | 2.43 | 5.1 |
| 140.7 | 50.0 | 2.36 | 7.8 |

Example 30

Temperature Effects on Neutralization of Crude Product with Tetra-n-Butylammonium Hydroxide ("TBAH").

The method and apparatus described in Example 1 were used to determine temperature effects on neutralization of crude product with an aqueous solution of TBAH. Results of pH measurement for each run are presented in the following table:

| T | μL 1.1% TBAH | pH | % off target |
|---|---|---|---|
| 22.5 | 90.0 | 2.65 | 0.0 |
| 100.3 | 90.0 | 2.55 | 3.8 |
| 140.7 | 90.0 | 2.48 | 6.4 |

Example 31

Temperature Effects on Neutralization of Crude Product with Triethylamine ("TEA").

The method and apparatus described in Example 1 were used to determine temperature effects on neutralization of crude product with an aqueous solution of TEA. Results of pH measurement for each run are presented in the following table:

| T | μL 1.0% TEA | pH | % off target |
|---|---|---|---|
| 22.5 | 60.0 | 2.63 | 0.0 |
| 100.3 | 60.0 | 2.51 | 4.6 |
| 140.5 | 60.0 | 2.50 | 4.9 |

Example 32

Temperature Effects on Neutralization of Crude Product with Diisopropylamine ("Di-i-PrNH2").

The method and apparatus described in Example 1 were used to determine temperature effects on neutralization of crude product with a cumene solution of Di-i-PrNH2. Results of pH measurement for each run are presented in the following table:

| T | μL 0.5% Di-i-PrNH2 | pH | % off target |
|---|---|---|---|
| 22.5 | 100.0 | 2.62 | 0.0 |
| 100.1 | 100.0 | 2.46 | 6.1 |
| 140.8 | 100.0 | 2.33 | 11.1 |

Example 33

Temperature Effects on Neutralization of Crude Product with Ammonium Hydroxide.

The method and apparatus described in Example 1 were used to determine temperature effects on neutralization of crude product with ammonium hydroxide. Results of pH measurement for each run are presented in the following table:

| T | μL 0.33% NH$_4$OH | pH | % off target |
|---|---|---|---|
| 22.5 | 30.0 | 2.36 | 0.0 |
| 100.2 | 30.0 | 2.05 | 13.1 |
| 140.3 | 30.0 | 1.49 | 36.9 |

Example 34

Temperature Effects on Neutralization of Crude Product with Sodium Hydroxide.

The method and apparatus described in Example 1 were used to determine temperature effects on neutralization of crude product with aqueous solutions of sodium hydroxide. Results of pH measurement for each run are presented in the following tables:

| T | μL 0.8% NaOH | pH | % off target |
|---|---|---|---|
| 22.5 | 30.0 | 2.71 | 0.0 |
| 140.3 | 30.0 | 2.51 | 7.4 |

| T | μL 0.4% NaOH | pH | % off target |
|---|---|---|---|
| 22.5 | 60.0 | 2.49 | 0.0 |
| 100.5 | 60.0 | 2.46 | 1.2 |
| 140.5 | 60.0 | 2.37 | 4.8 |

The preceding Examples are intended to describe certain preferred embodiments of the present invention. It should be appreciated, however, that obvious additions and modifications of the invention will be apparent to one skilled in the art. The invention is not limited except as set forth in the claims.

What is claimed is:

1. An improved method for production of phenol and acetone from cumene hydroperoxide by decomposition of cumene hydroperoxide in the presence of a mineral acid catalyst, wherein the improvement comprises neutralization of said mineral acid catalyst after substantial completion of said decomposition by addition of a substituted amine selected from the group consisting of:

(i) a secondary or tertiary amine having from 4 to 21 carbon atoms and not having hydrolytically unstable substituents or acidic substituents; and (ii) a primary amine of formula

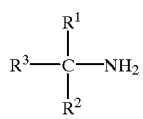

wherein $R^1$ and $R^2$ are independently $C_1-C_{12}$ alkyl, and $R^3$ is $C_1-C_{12}$ alkyl or $C_1-C_{12}$ alkyl substituted by hydroxyl, amino or dimethylamino,
said neutralization being performed at a temperature in the range from 115° C. to 180° C.,
said neutralization being performed to a final pH in the range from about 2.0 to 3.5.

2. The method of claim 1 in which said secondary or tertiary amine is selected from the group consisting of

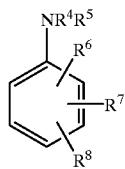

wherein $R^4$ and $R^5$ are independently hydrogen or methyl, and $R^6$, $R^7$ and $R^8$ are independently hydrogen or $C_1-C_4$ alkyl;

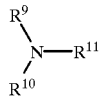

wherein $R^9$ and $R^{10}$ are independently $C_1-C_{12}$ alkyl, $C_2-C_{12}$ alkyl substituted by hydroxyl, amino or dimethylamino, $C_3-C_7$ alkylene or $R^9$ and $R^{10}$ join with $NR^{11}$ to form a cyclic aliphatic amine having from 5 to 7 ring atoms, and $R^{11}$ is hydrogen, $C_2-C_{12}$ alkyl, $C_2-C_{12}$ alkyl substituted by hydroxyl, $C_5-C_6$ cycloalkyl or $C_3-C_7$ alkylene, provided that $R^9$, $R^{10}$ and $R^{11}$ taken together contain at least six carbon atoms; and

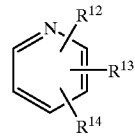

wherein $R^{12}$, $R^{13}$ and $R^{14}$ are independently hydrogen or $C_1-C_4$ alkyl.

3. The method of claim 1 in which said substituted amine is

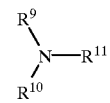

wherein $R^9$ and $R^{10}$ are independently $C_2-C_6$ alkyl or $C_2-C_6$ alkyl substituted by hydroxyl, or $R^9$ and $R^{10}$ join with $NR^{11}$ to form a cyclic aliphatic amine having from 6 to 7 ring atoms; and $R^{11}$ is hydrogen, $C_2-C_6$ alkyl or $C_2-C_6$ alkyl substituted by hydroxyl.

4. The method of claim 3 in which $R^9$, $R^{10}$ and $R^{11}$ are independently $C_2-C_6$ alkyl or $C_2-C_6$ alkyl substituted by hydroxyl.

5. The method of claim 4 in which said neutralization is performed to a final pH in the range from about 2.2 to about 2.8.

6. The method of claim 1 in which $R^1$ and $R^2$ are independently $C_1-C_9$ alkyl, and $R^3$ is $C_2-C_9$ alkyl.

7. The method of claim 6 which $R^1$ and $R^2$ are methyl and $R^3$ is $C_3-C_9$ alkyl.

8. The method of claim 7 in which $R^1$ and $R^2$ are methyl and $R^3$ is $C_5-C_9$ alkyl.

9. The method of claim 8 in which said neutralization is performed to a final pH in the range from about 2.2 to about 2.8.

* * * * *